US008852210B2

(12) United States Patent
Selover et al.

(10) Patent No.: US 8,852,210 B2
(45) Date of Patent: Oct. 7, 2014

(54) RIGIDLY GUIDED IMPLANT PLACEMENT

(75) Inventors: Sean Selover, Westport, MA (US); Christopher W. Sicvol, Boston, MA (US); Ronald Naughton, Tiverton, RI (US); Nancy M. Sheehy, South Boston, MA (US); Paul Birkmeyer, Marshfield, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/453,421

(22) Filed: Apr. 23, 2012

(65) Prior Publication Data

US 2012/0209290 A1  Aug. 16, 2012

Related U.S. Application Data

(63) Continuation of application No. 10/913,178, filed on Aug. 6, 2004, now Pat. No. 8,182,491.

(51) Int. Cl.
| | |
|---|---|
| *A61B 19/00* | (2006.01) |
| *A61B 17/58* | (2006.01) |
| *A61B 17/60* | (2006.01) |
| *A61F 2/00* | (2006.01) |
| *A61F 2/46* | (2006.01) |
| *A61B 17/88* | (2006.01) |
| *A61B 17/34* | (2006.01) |

(52) U.S. Cl.
CPC ........... *A61B 19/201* (2013.01); *A61B 19/5244* (2013.01); *A61B 2017/3409* (2013.01); *A61B 19/26* (2013.01); *A61B 2019/507* (2013.01); *A61B 2019/5255* (2013.01); *A61B 2019/202* (2013.01)
USPC ........... 606/130; 606/86 R; 606/279; 606/104

(58) Field of Classification Search
CPC ...................................................... A61B 19/201
USPC ................................ 606/86 R, 104, 130, 279
See application file for complete search history.

(56) References Cited

U.S. PATENT DOCUMENTS

| | | | |
|---|---|---|---|
| 2,919,599 A | 1/1960 | Milton et al. | |
| 5,016,489 A | 5/1991 | Yoda | |
| 5,184,601 A | 2/1993 | Putman | |
| 5,212,720 A | 5/1993 | Landi et al. | |
| 5,236,432 A | 8/1993 | Matsen, III et al. | |
| 5,250,055 A | 10/1993 | Moore et al. | |

(Continued)

FOREIGN PATENT DOCUMENTS

| | | |
|---|---|---|
| EP | 0654244 B1 | 5/1995 |
| EP | 1018963 B1 | 7/2000 |

(Continued)

*Primary Examiner* — David Bates
(74) *Attorney, Agent, or Firm* — Nelson Mullins Riley & Scarborough LLP

(57) ABSTRACT

A system for guiding an implant to an optimal placement within a patient includes a trajectory guide for guiding instruments along a selected trajectory and a trajectory fixation device for fixing the trajectory guide in a selected position. The trajectory guide defines a path configured to align with the selected trajectory. A movable support mounts the trajectory guide and selectively moves the trajectory guide to align the trajectory guide with the selected trajectory prior to fixing the trajectory guide in the selected position. After fixing the trajectory guide, instruments can be inserted along the trajectory through the path defined by the trajectory guide.

7 Claims, 13 Drawing Sheets

(56) References Cited

U.S. PATENT DOCUMENTS

| | | | |
|---|---|---|---|
| 5,397,323 A | 3/1995 | Taylor et al. | |
| 5,410,638 A | 4/1995 | Colgate et al. | |
| 5,433,198 A * | 7/1995 | Desai | 600/374 |
| 5,445,166 A | 8/1995 | Taylor | |
| 5,808,665 A | 9/1998 | Green | |
| 5,810,841 A | 9/1998 | McNeirney et al. | |
| 5,814,038 A | 9/1998 | Jensen et al. | |
| 5,855,583 A | 1/1999 | Wang et al. | |
| 5,957,933 A | 9/1999 | Yanof et al. | |
| 5,961,527 A | 10/1999 | Whitmore, III et al. | |
| 6,059,790 A | 5/2000 | Sand et al. | |
| 6,071,295 A * | 6/2000 | Takahashi | 606/191 |
| 6,096,049 A | 8/2000 | McNeirney et al. | |
| 6,120,465 A | 9/2000 | Guthrie et al. | |
| 6,159,179 A | 12/2000 | Simonson | |
| 6,206,890 B1 | 3/2001 | Truwit | |
| 6,246,200 B1 | 6/2001 | Blumenkranz et al. | |
| 6,298,262 B1 | 10/2001 | Franck et al. | |
| 6,334,067 B1 | 12/2001 | Brabrand | |
| 6,351,662 B1 | 2/2002 | Franck et al. | |
| 6,409,735 B1 | 6/2002 | Andre et al. | |
| 6,529,765 B1 | 3/2003 | Franck et al. | |
| 6,546,277 B1 | 4/2003 | Franck et al. | |
| 6,546,279 B1 | 4/2003 | Bova et al. | |
| 6,575,899 B1 | 6/2003 | Foley et al. | |
| 6,626,830 B1 * | 9/2003 | Califiore et al. | 600/229 |
| 6,725,080 B2 | 4/2004 | Melkent et al. | |
| 6,796,988 B2 | 9/2004 | Melkent et al. | |
| 6,837,892 B2 | 1/2005 | Shoham et al. | |
| 6,872,213 B2 | 3/2005 | Chakeres | |
| 6,921,406 B1 | 7/2005 | Chakeres | |
| 6,929,606 B2 | 8/2005 | Ritland | |
| 6,949,105 B2 | 9/2005 | Bryan et al. | |
| 6,951,538 B2 | 10/2005 | Ritland | |
| 2001/0027271 A1 | 10/2001 | Franck et al. | |
| 2002/0035321 A1 | 3/2002 | Bucholz et al. | |
| 2002/0038118 A1 | 3/2002 | Shoham | |
| 2002/0123668 A1 | 9/2002 | Ritland | |
| 2003/0149430 A1 | 8/2003 | Ferrante et al. | |
| 2003/0167061 A1 | 9/2003 | Schlegel et al. | |
| 2003/0187431 A1 | 10/2003 | Simonson | |
| 2003/0189351 A1 | 10/2003 | Nakayama et al. | |
| 2003/0236447 A1 | 12/2003 | Ritland | |
| 2004/0049191 A1 | 3/2004 | Markworth et al. | |
| 2004/0158260 A1 | 8/2004 | Blau et al. | |
| 2004/0176779 A1 | 9/2004 | Casutt et al. | |
| 2005/0033315 A1 | 2/2005 | Hankins | |
| 2005/0070789 A1 * | 3/2005 | Aferzon | 600/424 |
| 2005/0085714 A1 | 4/2005 | Foley et al. | |
| 2005/0101866 A1 * | 5/2005 | Goodwin | 600/449 |
| 2005/0113809 A1 | 5/2005 | Melkent et al. | |
| 2005/0132837 A1 | 6/2005 | Ben Horin et al. | |
| 2005/0149054 A1 | 7/2005 | Gorek | |
| 2005/0171551 A1 * | 8/2005 | Sukovich et al. | 606/86 |
| 2005/0171557 A1 | 8/2005 | Shoham | |
| 2005/0171559 A1 | 8/2005 | Chakeres | |
| 2005/0216026 A1 | 9/2005 | Culbert | |
| 2006/0036264 A1 | 2/2006 | Selover et al. | |
| 2007/0055291 A1 | 3/2007 | Birkmeyer et al. | |

FOREIGN PATENT DOCUMENTS

| | | |
|---|---|---|
| WO | 03/009768 A1 | 2/2003 |
| WO | 03/105659 A2 | 12/2003 |
| WO | 2004/100758 A2 | 11/2004 |
| WO | 2005/009215 A2 | 2/2005 |
| WO | 2005/032325 A2 | 4/2005 |

* cited by examiner

RIGIDLY GUIDED IMPLANT PLACEMENT

RELATED APPLICATIONS

This application is a continuation application of U.S. patent application Ser. No. 10/913,178 entitled "RIGIDLY GUIDED IMPLANT PLACEMENT," filed on Aug. 6, 2004, the contents of which are hereby incorporated by reference.

FIELD OF THE INVENTION

The present invention relates to spinal fixation devices used in orthopedic surgery. More particularly, the present invention relates to instrumentation and a method for the optimal placement of surgical implements and implants.

BACKGROUND OF THE INVENTION

Spinal fixation systems may be used in orthopedic surgery to align, stabilize and/or fix a desired relationship between adjacent vertebral bodies. Such systems typically include a spinal fixation element, such as a relatively rigid fixation rod or plate, extending along an axis along which the vertebral bodies are to be positioned and coupled to adjacent vertebrae by attaching the element to various anchoring devices, such as hooks, bolts, wires or screws. The spinal fixation element can have a predetermined contour that has been designed according to the properties of the target implantation site and, once installed, the spinal fixation element holds the vertebrae in a desired spatial relationship, either until desired healing or spinal fusion has occurred, or for some longer period of time.

Spinal fixation elements can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone, which is the strongest part of the vertebrae. Such screws typically include a threaded shank that is adapted to be threaded into a vertebra, and a head portion having a spinal fixation element receiving element, which, in spinal rod applications, is usually in the form of a U-shaped slit formed in the head for receiving the rod. In many pedicle screws, the head is movable and preferably pivotable in all directions, relative to the shaft. The ability to move the head relative to the anchoring portion of the screw facilitates alignment and seating of a rod connecting a plurality of screws A set-screw, plug, cap or similar type of closure mechanism may be used to lock the rod into the rod-receiving portion of the pedicle screw. In use, the shank portion of each screw is then threaded into a vertebra, and once properly positioned, a fixation rod is seated through the rod-receiving portion of each screw and the rod may be locked in place by tightening a cap or similar type of closure mechanism to securely interconnect each screw and the fixation rod. Other anchoring devices include hooks and other types of bone screws Placement of pedicle screws in a percutaneous fashion has become desirable for all minimally invasive approaches to the spine. This technique generally relies heavily on a clear understanding of the local anatomy by the surgeon, as well as accurate radiographic guidance technology. Generally, placement is done using a large bore needle or a canulated drill to start an initial hole for screw placement. Pedicle screws are preferably threaded in alignment with the pedicle axis and inserted along a trajectory that is determined prior to insertion of the screws. Misalignment of the pedicle screws during insertion can cause the screw body or its threads to break through the vertebral cortex and be in danger of striking surrounding nerve roots. A variety of undesirable symptoms can easily arise when the screws make contact with nerves after breaking outside the pedicle cortex, including dropped foot, neurological lesions, sensory deficits, or pain.

The placement of pedicle screws and other implants requires a high degree of accuracy and precision to ensure a proper trajectory for the implant. It is preferable that each instrument used in the process be inserted along the same trajectory to ensure proper placement. Known surgical procedures for inserting pedicle screws involve recognizing landmarks along the spinal column for purposes of locating optimal screw hole entry points, approximating screw hole trajectories, and estimating proper screw hole depth. Generally, large amounts of fluoroscopy are required to determine a proper pedicle screw trajectory and to monitor the advancement of a pedicle screws through the vertebra. However, prolonged radiation exposure to a patient and a surgeon is undesirable.

More technologically advanced systems such as the StealthStation™ Treatment Guidance System, the FluoroNav™ Virtual Fluoroscopy System (both available from Medtronic Sofamor Danek), and related systems, seek to overcome the need for surgeons to approximate landmarks, angles, and trajectories, by assisting the surgeons in determining proper tap hole starting points, trajectories, and depths. However, these systems are extremely expensive, require significant training, are cumbersome in operation, are difficult to maintain, and are not cost effective for many hospitals.

U.S. Pat. No. 6,725,080 describes an image-guided surgical navigation system including a tool guide that uses a trackable marker. The surgeon must manually position of the tool guide and maintain the position of the tool guide during surgery through the use of image guidance and computer software. Therefore, the position of the tool guide is subject to human error, fatigue and slippage, and requires continued operation of expensive equipment and prolonged exposure to radiation to maintain.

SUMMARY OF THE INVENTION

The present invention provides a system and method for guiding an implant to an optimal placement within a patient. The system includes a trajectory guide for guiding and restricting instruments along a selected trajectory and a trajectory fixation device for fixing the trajectory guide in a selected position relative to the patient. A movable support mounts the trajectory guide and selectively moves the trajectory guide to align the trajectory guide with the selected trajectory prior to fixing the trajectory guide in the selected position.

According to a first aspect of the invention, a guidance system for use while inserting an implant is provided. The guidance system comprises a trajectory guide defining a path configured to align with a trajectory for guiding instruments along the trajectory and a lock for locking the trajectory guide in a selected orientation relative to a patient. The trajectory guide restricts the instruments to movement along the trajectory.

According to another aspect of the invention, a method for guiding an implant comprises the steps of determining a suitable trajectory for inserting the implant and fixing the trajectory relative to a patient using a trajectory guide. The trajectory guide is fixed at a fixation point located outside the body of the patient.

According to still another aspect, a method of inserting a pedicle screw into a pedicle bone of a patient is provided. The method comprises the steps of aligning a channel of a trajectory guide with a pedicle screw trajectory, locking the trajectory guide in an aligned position, inserting a first instrument through the trajectory guide to create a hole in the pedicle bone aligned with the pedicle screw trajectory, and inserting a pedicle screw through the trajectory guide and into the hole.

In yet another aspect of the invention, a surgical kit for inserting an implant is provided. The surgical kit comprises a first instrument for preparing a surgical site to receive the implant, a second instrument for inserting the implant in prepared surgical site and a trajectory guide for guiding said first instrument and second instrument along a trajectory. The first instrument and the second instrument are sized and configured to fit the trajectory guide.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principals of the invention and, although not to scale, show relative dimensions.

DETAILED DESCRIPTION

The present invention provides an improved guidance system and method for guiding an implant, such as a pedicle screw, along a predetermined trajectory. The present invention will be described below relative to an illustrative embodiment. Those skilled in the art will appreciate that the present invention may be implemented in a number of different applications and embodiments and is not specifically limited in its application to the particular embodiments depicted herein.

The guidance system of an illustrative embodiment of the invention is used to insert a pedicle screw into a vertebra, though one skilled in the art will recognize that the invention can be used to place any suitable implant that requires a known trajectory. Examples of surgical procedures suitable for employing the guidance system of the present invention include, but are not limited to, insertion of interbody fusion devices, bone anchors, fixation devices, including rods, plates and cables, artificial disks and hip stems. The guidance system can be used to position any suitable implant, instrument and/or other device in any suitable procedure where guidance of the implant, instrument and/or device is key.

Figure 1:
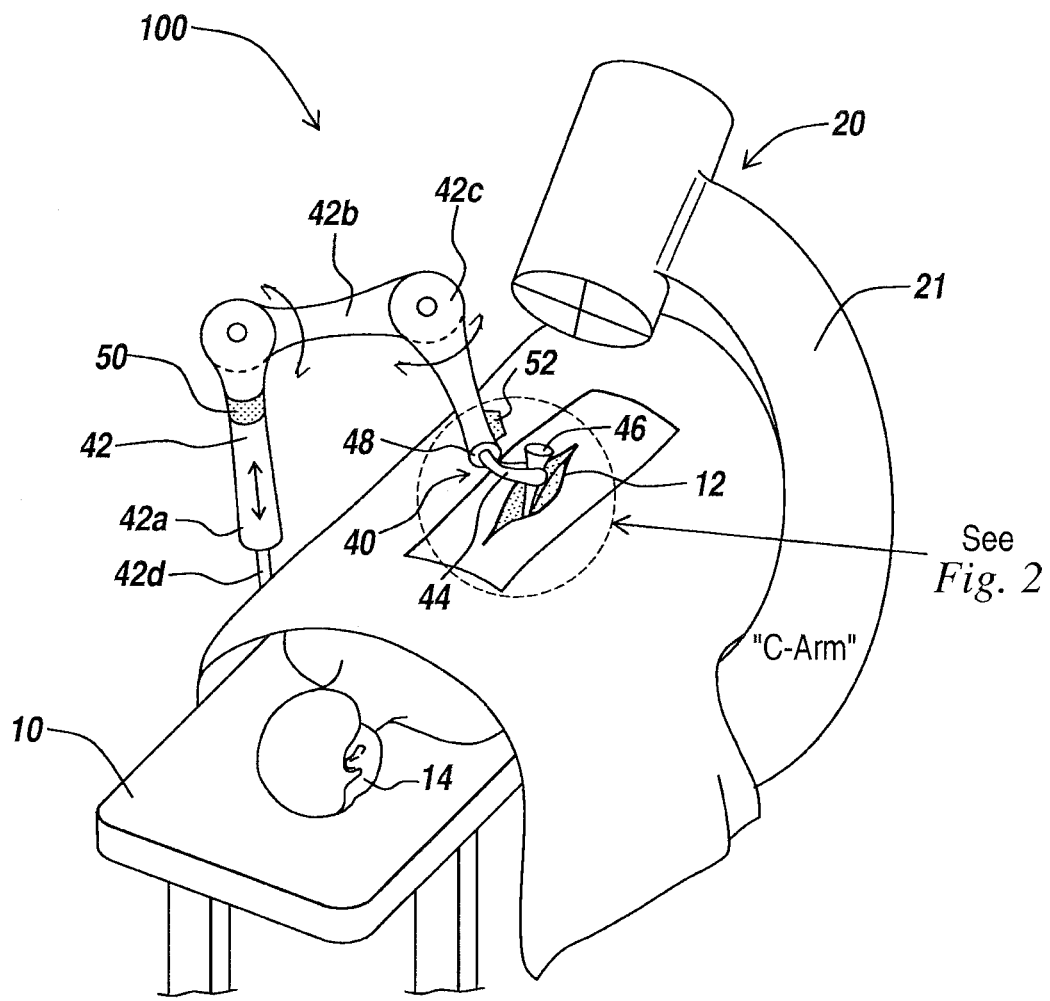
FIG. 1 illustrates a guidance system for guiding instruments used in a medical procedure according to an illustrative embodiment of the invention.

Referring to FIG. 1, a guidance system 100 of an illustrative embodiment of the invention facilitates placement of an implant, such as a pedicle screw, in a patient while minimizing radiation exposure. The guidance system 100 includes a trajectory guide 40 for guiding instruments used in performing a medical procedure into a surgical site along a selected trajectory and restricting the degree of motion of the instruments to movement along the selected trajectory. An imaging system 20, illustrated as a fluoroscopy unit 21, is provided for initially locating a suitable trajectory for the instruments used in performing a medical procedure, for example, instruments used to prepare an implant site and/or inserting an implant into the implant site. The system 100 may include an operating table 10 for positioning a patient 14 in a prone position to expose the surgical site 12 to the imaging system 20 and trajectory guide 40. As shown, the trajectory guide 40 is positioned outside of the patient's body.

Examples of instruments used to prepare an implant site and/or place an implant into a surgical site include, but are not limited to awls, bone taps, obturators, drills, guide wires and implants, such as screws, fusion devices, artificial disks and hip stems. One skilled in the art will recognize that the trajectory guide 40 is not limited to use with instruments used to prepare an implant site and/or place an implant into a surgical site and that the trajectory guide can be used to guide any suitable instrument used in a medical procedure along a selected trajectory.

The trajectory guide 40 can be any suitable device defining a path for guiding a surgical instrument, device and/or implant. The illustrative trajectory guide 40 includes a cannula 46 defining a path therethrough configured to align with the trajectory, though one skilled in the art will recognize that any suitable guide means may be used. The trajectory guide can have any suitable cross-section and is not limited to the cylindrical cross-section shown in the illustrative embodiments. The trajectory guide can be open or closed to define an open or closed path therethrough.

Figure 2:
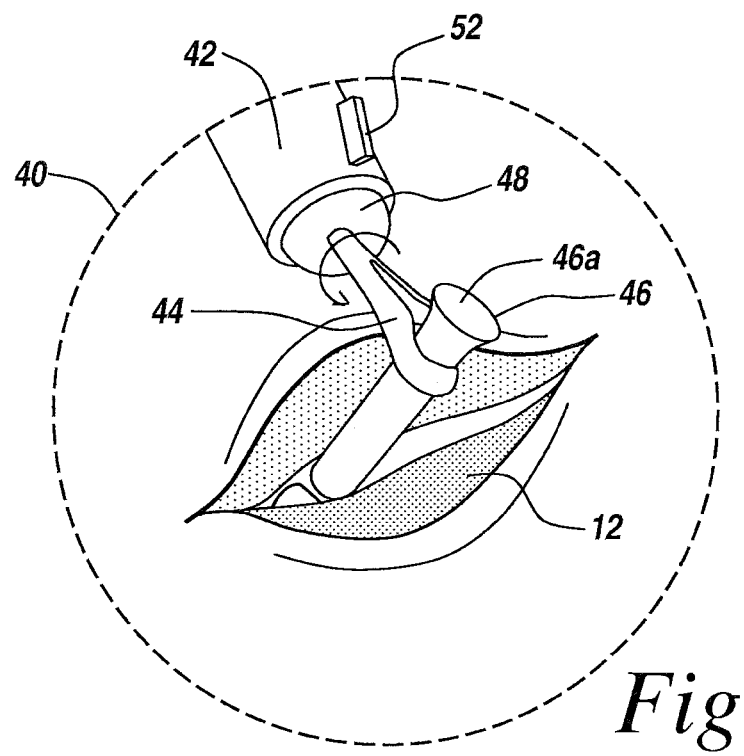
FIG. 2 is a detailed view of the trajectory guide of FIG. 1.

The cannula 46 can be spaced from or directly interface with the surgical site 12. The path through the cannula 46 forms a working channel configured to receive and guide selected surgical instruments along the longitudinal axis thereof. The cannula 46 preferably prevents the instruments from moving in any direction other than along the trajectory. The trajectory guide 40 further includes a movable guide support for moving the cannula 46 into a selected position relative to the patient in alignment with the trajectory and selectively locking the aligned cannula 46 in the selected position. The movable guide support includes a clamp 44 for holding the cannula 46 coupled to a distal end of a flexible arm 42 capable of selectively moving the clamp 44 in three dimensions to align the cannula 46 with a selected trajectory. A joint 48 may be provided for connecting the clamp 44 to the arm 42. FIG. 2 is a detailed view of the distal end of the trajectory guide 40 in the vicinity of the surgical opening 12 for the implant site on the patient. The flexible arm 42 allows the surgeon to bring the cannula 46 into the vicinity of the surgical site, while the joint 48 allows for fine-tuning of the orientation of the cannula 46.

The flexible arm 42 can comprise any suitable device for controlling the position and orientation of the trajectory guide 40 relative to the patient. As shown in FIG. 1, the flexible arm 42 comprises plurality of segments 42a, 42b, 42c pivotally connected together and mounted to a stand (not shown), the operating table 10, or other stable support. The first segment 42a is movably coupled to and slideably relative to a fixed shaft 42d though any suitable means, to allow the flexible arm to move along a vertical axis to raise or lower the flexible arm 42 relative to the operating table 10. The second segment 42b is pivotally coupled to the first segment 42a to provide a second degree of motion, while the third segment 42c is pivotally coupled to the second segment 42b to provide a third degree of motion. The clamp 44 and joint 48 cooperate to movably mount the cannula 46 or other suitable guide to the end of the third segment 42c. The use of a plurality of movably connected segments allows for the surgeon to move the cannula 46 in three dimensions. The flexible arm brings the trajectory guide into vicinity of an opening in the patient, while the joint 48 allows the surgeon to accurately position the cannula 46 at a selected angle relative to the patient.

Referring back to FIG. 2, according to an illustrative embodiment, the joint 48 is disposed at the distal end of the flexible arm 42 and comprises a ball joint having a wide degree of motion for orienting the cannula 46, though one skilled in the art will recognize that any suitable means for connecting the cannula to a movable support system may be used. The illustrative ball joint 48 provides a 160° cone of motion for positioning the cannula, though one skilled in the art will recognize that the ball joint 48 can have any suitable range of motion.

The clamp 44 extends from the ball joint 48 for holding the cannula in a selected position, as determined by the ball joint 48 and flexible arm 42. The clamp 44 can have any suitable size and configuration for rigidly holding the cannula 46 relative to the joint 48. The clamp 44 allows for the position of the trajectory to be fixed at a fixation point outside the body, rather than securing the trajectory guide at a location within the body by, for example, securing the trajectory guide to a body part. The use of an external fixation point facilitates positioning of the trajectory guide by the surgeon, while reducing the risk of infection to the patient.

The guidance system 100 further includes a least one cannula lock for locking the trajectory guide in a selected orientation relative to the patient. After a surgeon positions the cannula 46 in a selected orientation, such that a path through the cannula aligns with a previously determined trajectory, a lock or a series of locks associated with the movable guide support fixes the position of the cannula 46 to lock the trajectory. For example, the cannula lock can include at least one arm lock 50 and a joint lock 52. The arm lock 50, which can comprise a plurality of locks, each associated with an interface between two segments of the flexible arm 42, locks the flexible arm 42 in a selected position to secure the segments 42a, 42b, 42c, 42d relative to each other. The joint lock 52, when actuated, locks the joint 48 to the distal end of the third segment 42c to fix the cannula 46 relative to the flexible arm 42. The surgeon can manually actuate the cannula lock or automatically actuate the cannula lock to fix the position of the cannula 46 relative to the surgical site through any suitable means.

The locking mechanisms for the arm lock 50 and the joint lock 52 can comprise any suitable locking mechanism known in the art. Examples of suitable types of locking mechanisms include pneumatic locks, mechanical locks, such as set screws, clamps, collets and friction locks, electronic locks, magnetic locks, electromechanical locks, such as electromechanical locks utilizing a solenoid mechanism, and others known in the art.

Figure 3:
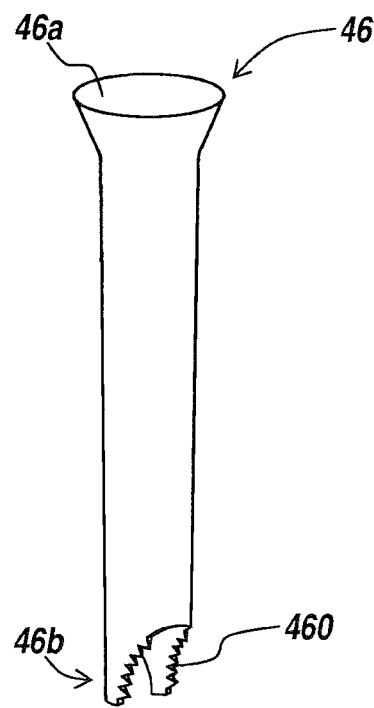
FIG. 3 is a side view of a cannula used in the trajectory guide of FIGS. 1 and 2

FIG. 3 is a side view of an embodiment of a cannula 46 for guiding instruments according to an embodiment of the invention. In the embodiment shown in FIGS. 1 and 2, the cannula 46 comprises a hollow tubular body suitable for insertion in and/or placement adjacent to a patient's body. The cannula 46 has at least one hollow channel or lumen defining a path extending from an open first end 46a of the cannula 46 to an open second end 46b of the cannula 46b. The cannula 46 can be formed of any suitable surgical material, such as, but not limited to, surgical stainless steel.

The tubular body 46 can be rigid, semi-rigid or flexible, and can have any suitable size, shape and configuration suitable for defining a trajectory for implant placement. In the illustrative embodiment, the cannula 46 is straight to define a straight trajectory. Alternatively, the cannula 46 can be curved or have any other suitable shape to define a curved or otherwise shaped trajectory. The cannula 46 is not limited to a tubular structure having closed sidewalls and can be any component that defines a path, including an open channel or a solid member.

As shown in FIG. 3, the second end 46b of the cannula 46 can be configured to interface with bone or another feature to facilitate positioning of the cannula 46 along a suitable trajectory relative to the surgical site. As shown, the cannula 46 can include teeth 460 formed on an outer surface of the lower end for engaging the pedicle bone.

The cannula 46 can have any suitable diameter suitable for guiding an instrument along a path defined by the cannula. According to one embodiment, the cannula 46 can be configured to receive an instrument within the channel. In this embodiment, the inner diameter of the cannula 46 is slightly larger than the outer diameter of the instrument guided by the cannula, so that the instrument can be inserted through the cannula while the side walls of the cannula maintain the instrument at a predetermined angle relative to the patient. Alternatively, an instrument to be guided by the cannula is configured to slide over the cannula 46, with the cannula 46 maintaining the orientation of the instrument as the instrument slides relative to the cannula. In this embodiment, the cannula 46 can have an outer diameter that is slightly less than an inner diameter of an instrument. One skilled in the art will recognize that the cannula 46 can have any suitable size and configuration for guiding an instrument along a selected trajectory.

In one embodiment, the cannula 46 includes one or more stops (not shown) for limiting the insertion depth of an instrument guided through the cannula 46. Each stop is configured to abut a corresponding protrusion or other feature on the instrument to prevent the instrument from moving past the stop, thereby limiting the insertion depth of the instrument.

Figure 4A:
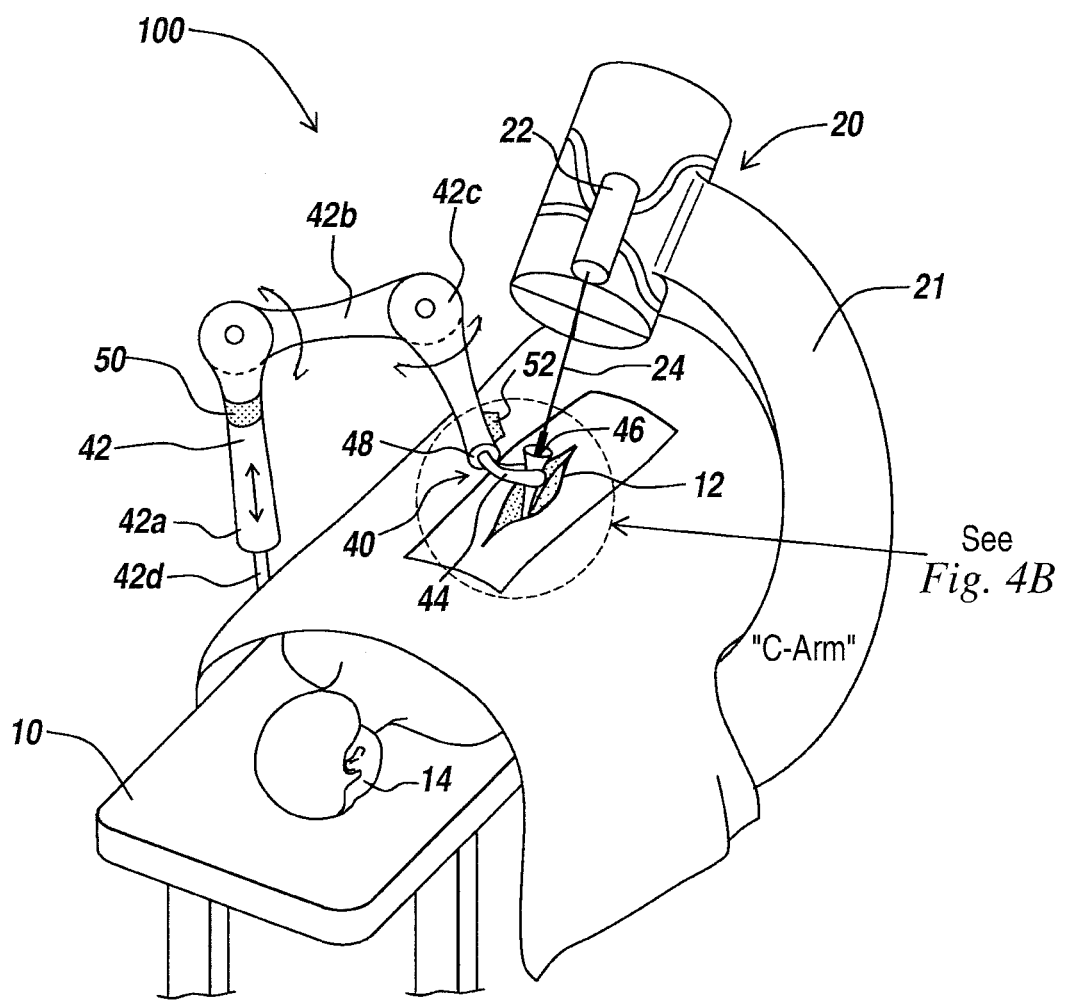
FIG. 4A illustrates a guidance system including a laser unit to assist in identifying a suitable trajectory according to an embodiment of the invention.
Figure 4B:
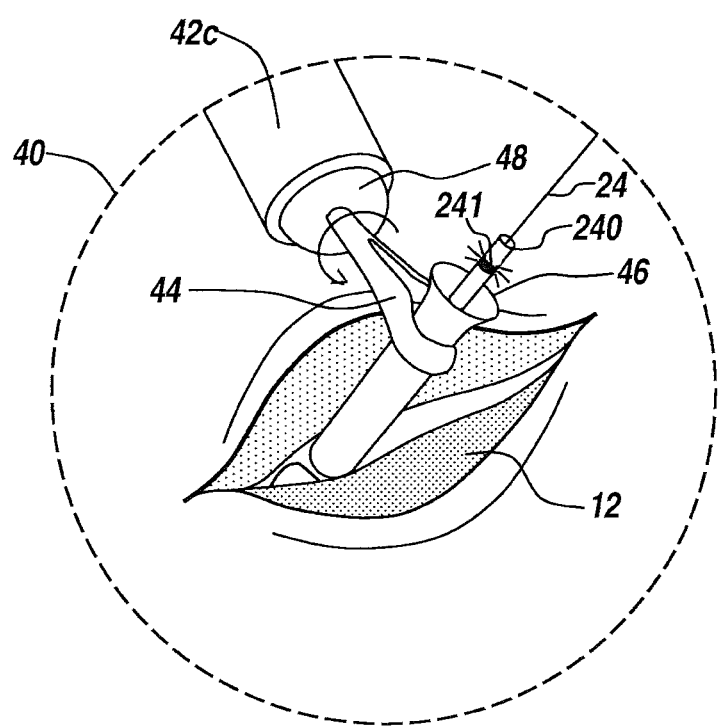
FIG. 4B is a detailed view of the trajectory guide of the system of FIG. 4A.

The imaging system 20 can comprise any suitable means for identifying a suitable trajectory for surgery and is not limited to a fluoroscopy unit 21. According to one embodiment, shown in FIGS. 4A and 4B, the fluoroscopy unit 21 can include a laser unit 22 for producing a light beam 24, for example, a focused light beam, for marking the trajectory after the fluoroscopy unit 21 identifies a suitable trajectory. As shown in FIG. 4B, the light beam 24 aligns with and extends through the cannula 46 when the cannula channel aligns with the trajectory. An orientation marker 240, configured to be inserted in the cannula 46, facilitates alignment of the light beam 24 with the path through the cannula 46. The orientation marker 240 can include one or more radiopaque portions 241, visible using fluoroscopy, to facilitate alignment.

According to the illustrative embodiment, the laser unit 22 for marking a trajectory comprises a Dual Radiation Targeting System (DRTS™) Platform system available from Min-Rad, Inc. of Buffalo, N.Y. Suitable systems for using a laser to identify a trajectory are described in U.S. Pat. Nos. 6,096,049, 5,810,841, 5,644,616 and 5,212,720, which are herein incorporated by reference in their entirety.

One skilled in the art will recognize that any suitable light source may be used to produce the light beam 23 and that the invention is not limited to a laser unit. For example, the imaging system 20 can employ an infrared light source, an incandescent light source or any suitable light source capable of producing a light beam marking a trajectory.

Figure 5A:
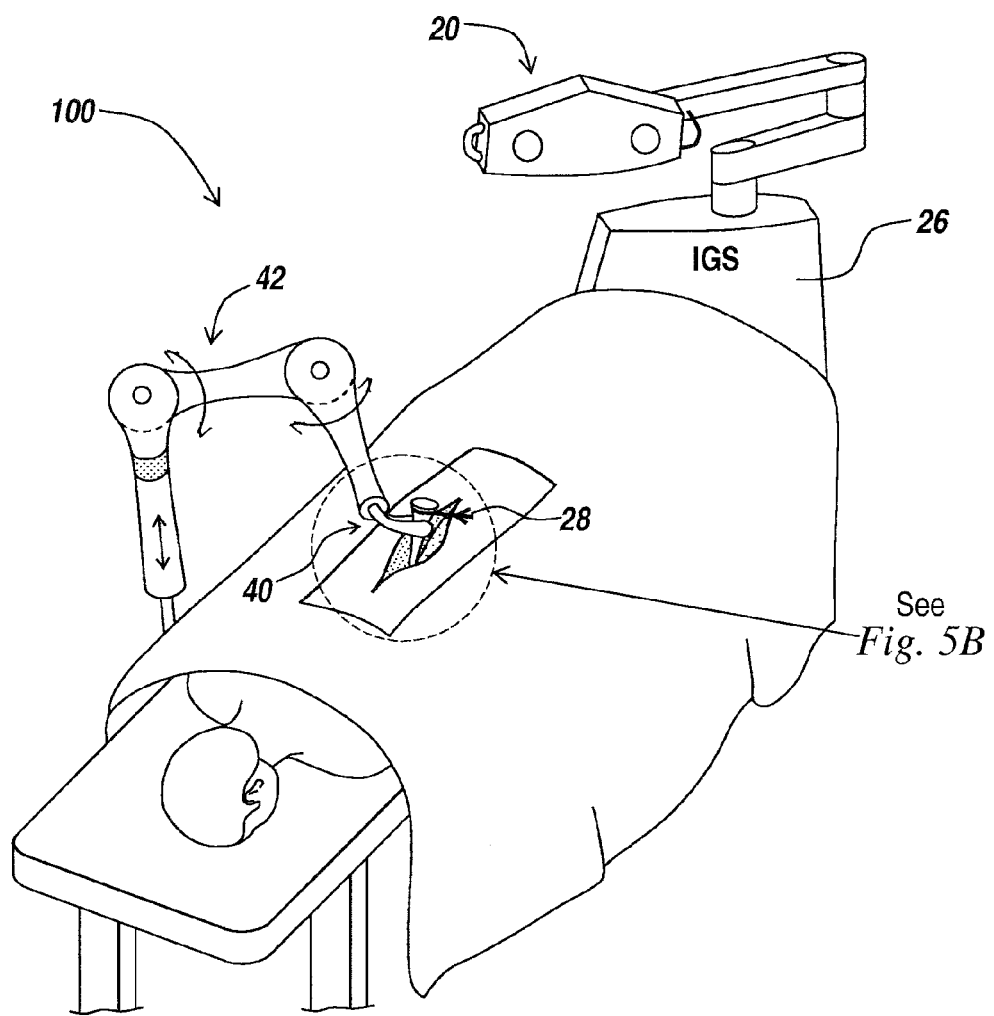
FIG. 5A illustrates a guidance system including an image guided surgery unit to assist in identifying a suitable trajectory according to an embodiment of the invention.
Figure 5B:
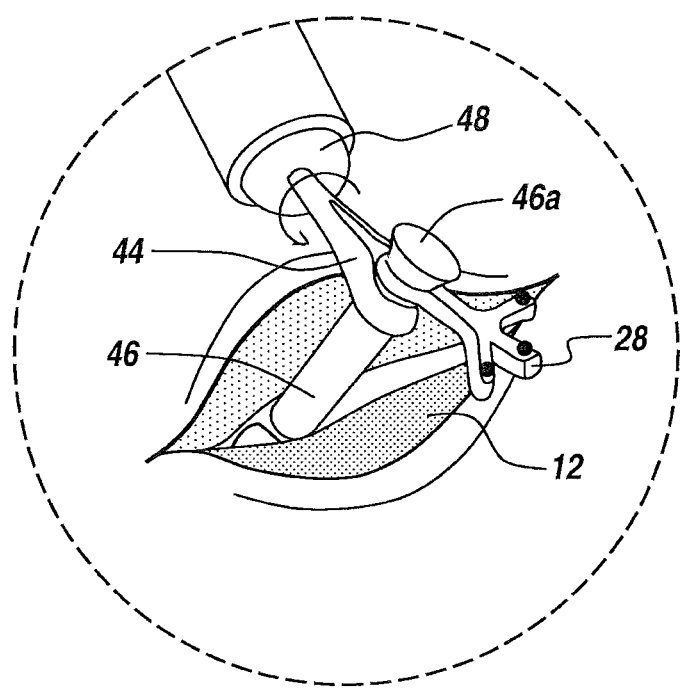
FIG. 5B is a detailed view of the trajectory guide of the system of FIG. 5A.

In another embodiment of the invention, as shown in FIGS. 5A and 5B, the imaging system 20 comprises an image-guided surgery unit 26. As shown in FIG. 5B, the guidance system 100 can include a 3-D array reference 28 to facilitate identification of a suitable trajectory. The 3-D array reference 28 is coupled to a proximal end 46a of the cannula 46 and cooperates with the image-guided surgery unit 26 to identify a suitable trajectory for implant placement and align the cannula 46 with the trajectory.

In one embodiment, the imaging system 20 employs the VectorVision® navigation system by BrainLab AG of Heimstetten Germany, which provides simultaneous navigation in CT and fluoroscopic images during surgery.

Figure 6A:
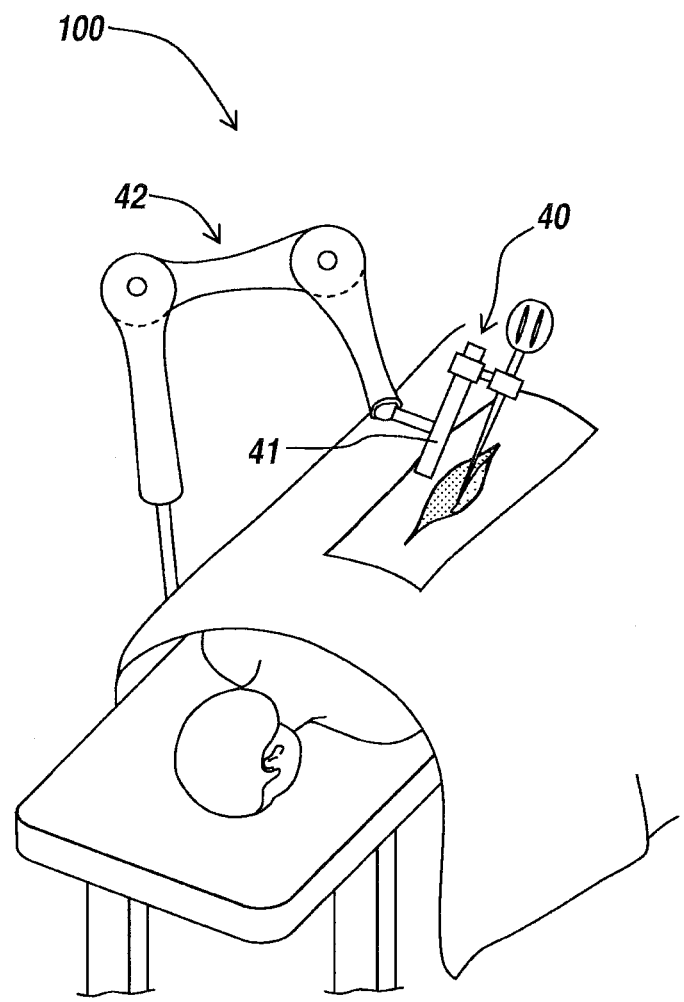
FIG. 6A illustrates a guidance system having a trajectory guide including a track according to an embodiment of the invention.
Figure 6B:
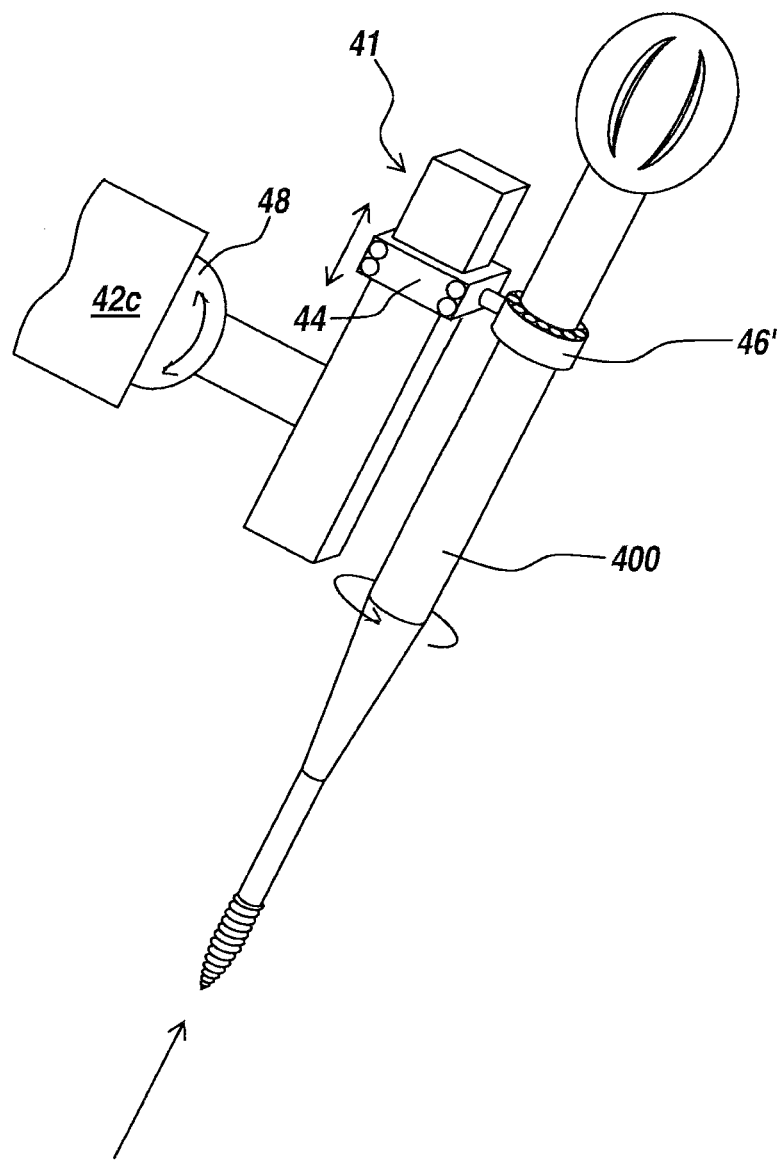
FIG. 6B is a detailed view of the trajectory guide of FIG. 6A.

According to one embodiment of the invention, as shown in FIGS. 6A and 6B, the trajectory guide 40 can include a track 41 configured to receive a clamp 44' connected to a cannula or an annular ring 46' defining the path for the instruments. In the embodiment shown in FIGS. 6A and 6B, the annular ring 46' holds a screw driver 400 in alignment with a selected trajectory. The annular ring 46' traverses the track 41, which allows the annular ring 46' to move along the trajectory after the trajectory guide fixes the trajectory by fixing the track 41 in a selected orientation. The user can move the instrument along the trajectory towards or away from pedicle, while the track maintains angular and spatial orientation of the instrument. The annular ring 46' and track 41 can allow instruments inserted therein to rotate on a fixed axis, facilitating insertion of an implant along the trajectory. One skilled in the art will recognize that any suitable means for moving the trajectory guide 40 along the trajectory may be used.

Figure 7:
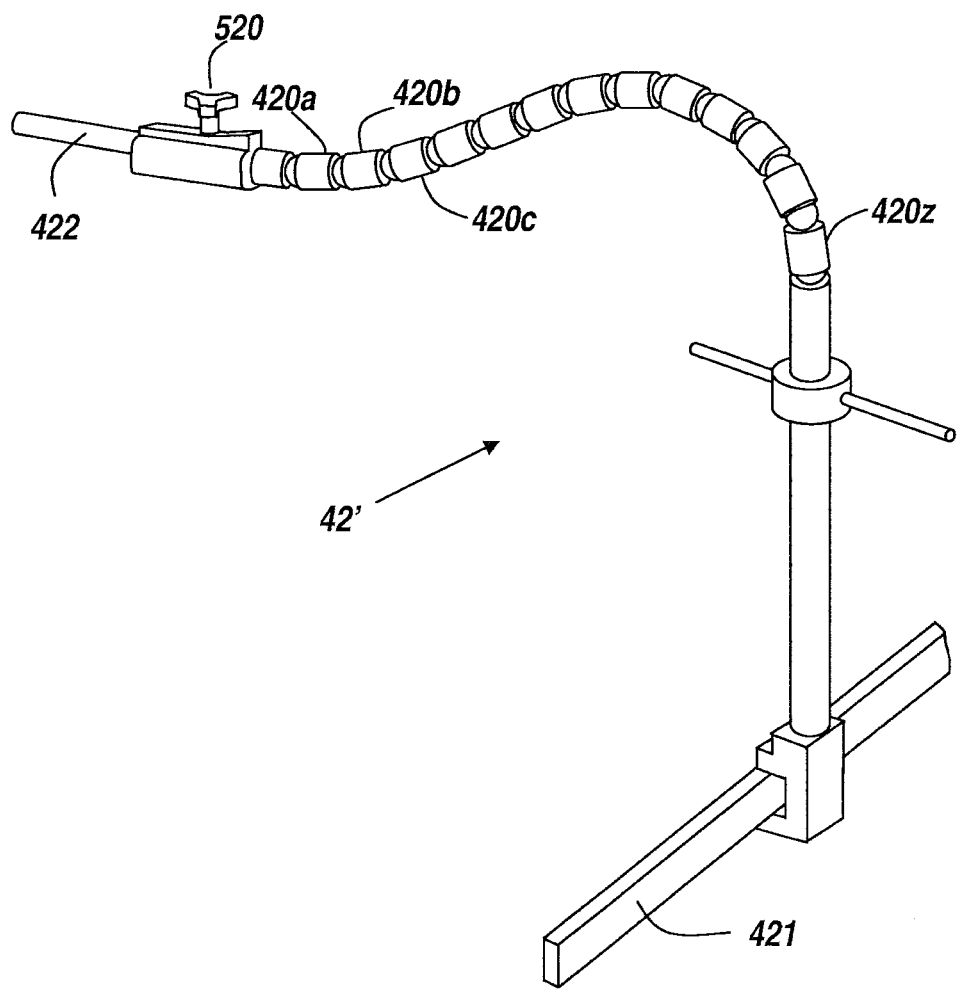
FIG. 7 illustrates a flexible arm suitable for use with the guidance system of FIG. 1 according to another embodiment of the invention.

FIG. 7 illustrates another embodiment of a flexible arm 42' suitable for use in the guidance system 100 of the present invention. The flexible arm 42' includes a plurality of movably linked segments 420a, 420b . . . 420z and a base 421 attached to the operating table. The flexible arm 42' includes a lock, illustrated as a three-lobed knob 520 located between the series 420 of linked segments and a joint segment 422, for locking the arm 42' and associated trajectory guide 40 in a selected position and orientation. The illustrative arm 42' "locks" down the series of linked segments 420 and the joint segment 422 when the knob 520 is turned clockwise. As the user turns the knob, the knob applies a force to rods located within the series of linked segments and the joint segment 422 to create an interference or friction fit at the joint between the series of linked segments and the joint segment 422. As the knob turns, the joint located at the knob is clamped tight by creating a high degree of friction between the two pieces. These friction fits immobilize all the linked segments to create a rigid arm. Turning the knob counter clockwise releases pressure induced on all the surfaces allowing the arm to become "flexible" again.

The flexible arm 42' illustrated in FIG. 7 is available from Mediflex® Surgical Products of Islandia, N.Y., though one skilled in the art will recognize that the flexible arm can have any suitable configuration, size and source.

Figure 8:
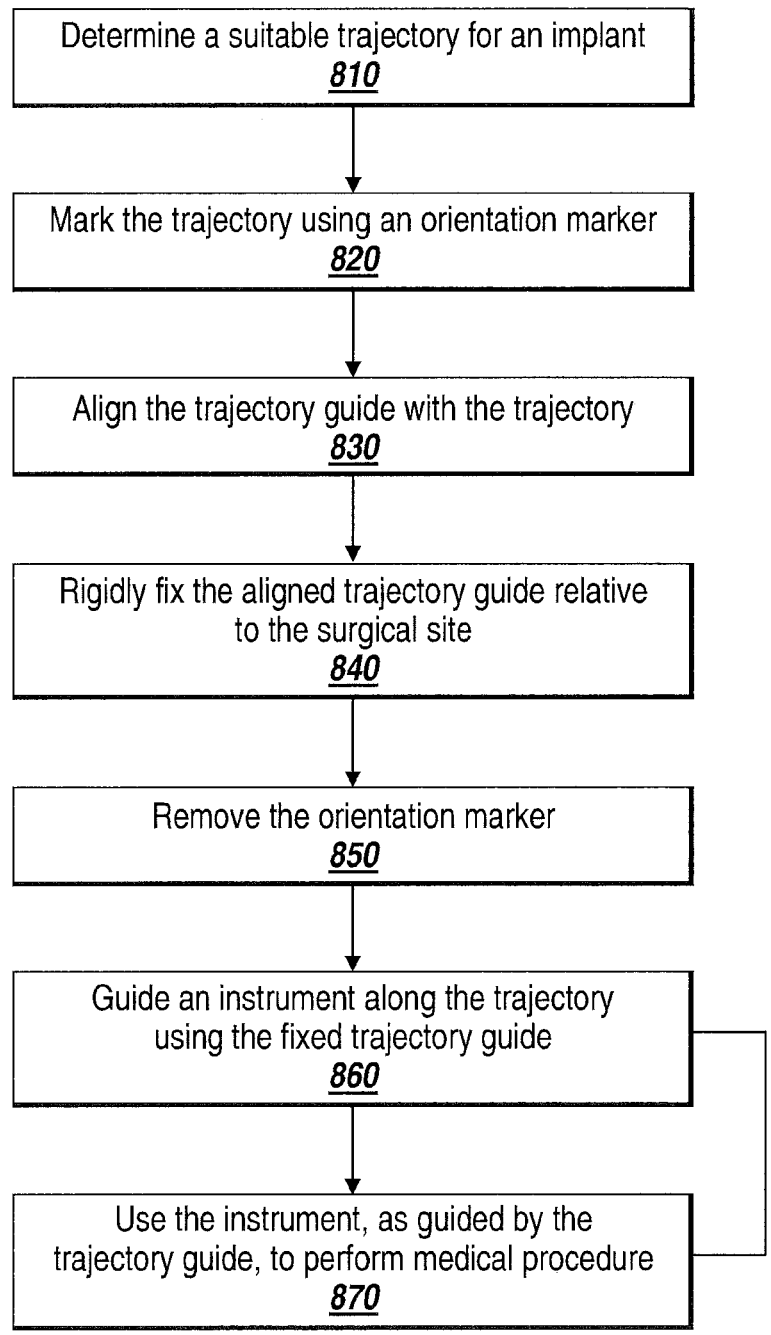
FIG. 8 is a flow chart diagraming the steps involved in using the guidance system of FIG. 1 to guide instruments and implants into a selected surgical site along a suitable trajectory.

FIG. 8 is a flow chart diagraming the steps involved in using the guidance system 100 of FIG. 1 to guide instruments and implants into a selected surgical site along a suitable trajectory with minimal radiation exposure. The illustrative guidance system 100 and method provide reproducible, simplified steps for accurately placing an implant in a patient.

In step 810, a surgeon first determines a suitable trajectory for an implant. The step of determining a trajectory involves identifying a potential orientation, i.e., the location and angle, of a surgical implant site, such as a pedicle, using any suitable technique. Examples of suitable techniques for determining a suitable trajectory include using a k-wire, fluoroscopy, MRI, laser navigation and image guided surgery. For example, a surgeon generally identifies a trajectory by placing a patient on the operating table 10 in a selected position, locating anatomical landmarks on the patient, for example, using fluoroscopy, and locating a suitable incision site over the disc space of the patient. One skilled in the art will recognize that any suitable device and/or method for determining a suitable trajectory may be used.

After determining a suitable trajectory in step 810, the surgeon can mark the trajectory using an orientation marker in step 820. Examples of suitable orientation markers include, but are not limited to, a laser, a needle, an awl and an obturator.

After marking the orientation, the surgeon aligns the trajectory guide 40 with the trajectory in step 830. According to the illustrative embodiment, the surgeon aligns the trajectory guide by first bringing the cannula 46 into the vicinity of the surgical site and the trajectory to the surgical site by moving the flexible arm 42 along one or more suitable axes. The user then moves the cannula relative to the flexible arm 42 until a path through the cannula 46 aligns with the trajectory and the cannula 46 defines the trajectory. In this step, the surgeon uses the orientation marker as a guide for alignment of the trajectory guide path with the trajectory defined in step 810. For example, the surgeon can place the cannula over the orientation marker to align the cannula with the trajectory.

After alignment, the surgeon rigidly fixes the aligned trajectory guide in the selected position, orientation and angle relative to the surgical site in step 840 so as to define a fixed, guided trajectory for the instruments used in inserting instruments for the implant and the implant itself.

After fixing the trajectory, the surgeon removes the orientation marker in step 850, leaving the trajectory guide in the selected position aligned with the trajectory.

In step 860, the surgeon guides an instrument along the trajectory using the fixed trajectory guide. The use of a fixed trajectory guide defining the trajectory allows the surgeon to guide the instruments along the specified trajectory without requiring fluoroscopy. In step 870, the user uses the instrument, as guided by the trajectory guide, to perform medical procedure, for example, to prepare the surgical site and/or to insert the implant along the trajectory. The user can repeat steps 860 and 870 using different instruments as necessary to perform the selected medical procedure. The trajectory guide, which remains fixed, ensures that each instrument travel along the same trajectory.

Figure 9:
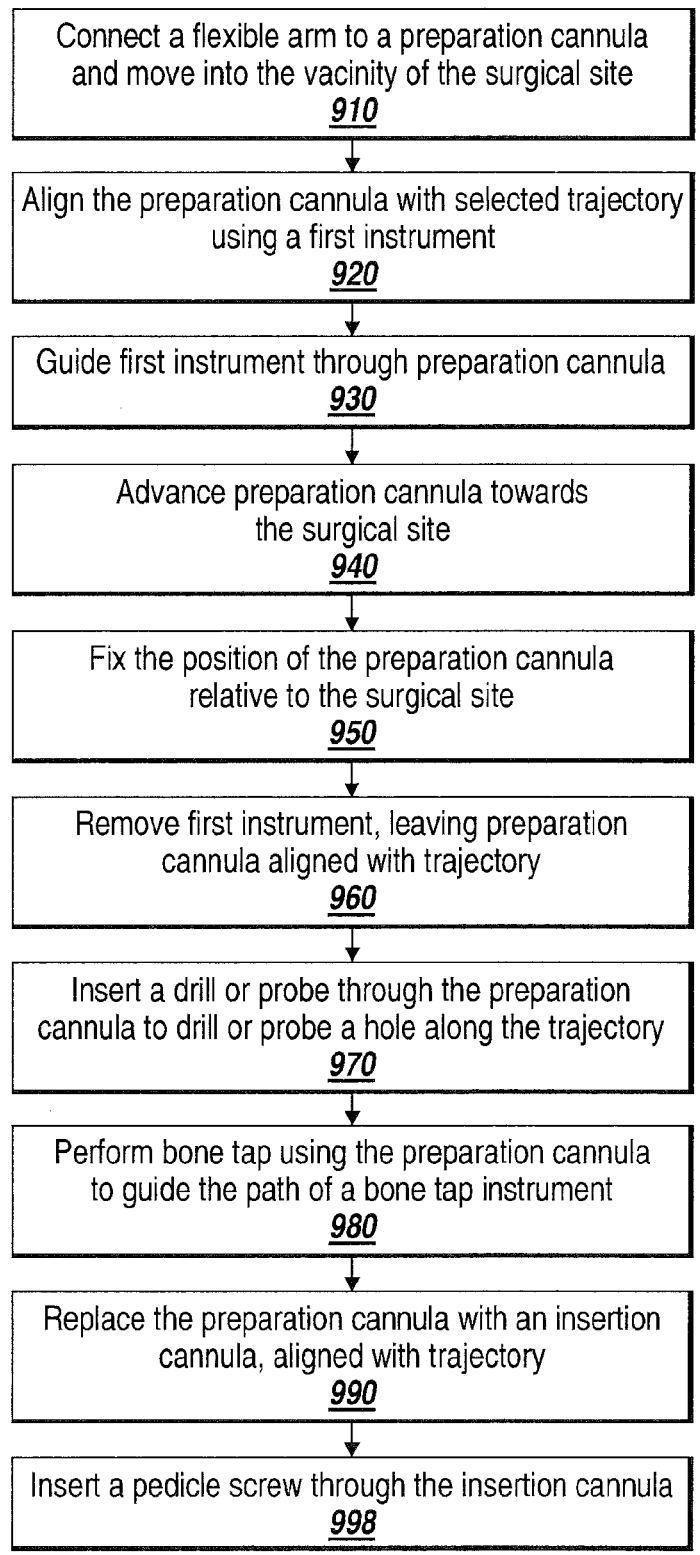
FIG. 9 is a flow chart diagraming the steps involved in using the guidance system of FIG. 1 prepare a pedicle and insert a pedicle screw along a trajectory.

FIG. 9 illustrates the steps involved in preparing a pedicle and inserting a pedicle screw into the prepared pedicle using the guidance system 100 of the illustrative embodiment of the invention. The illustrative method ensures proper pedicle screw placement with minimal radiation exposure. FIGS. 10A-10H illustrate the surgical site during each of the respective steps of FIG. 9. As shown, throughout the process, a trajectory guide maintains a trajectory T-T for guiding the pedicle instruments and the pedicle screw into the surgical site.

Figure 10A:
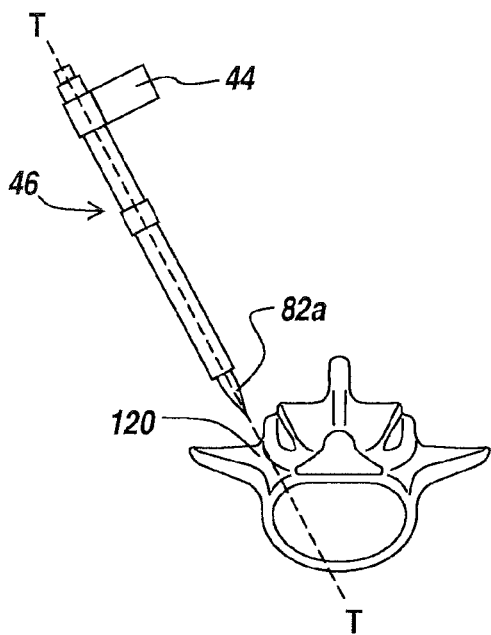
FIGS. 10A-10H illustrate the pedicle region during the steps shown in FIG. 9.

After identifying a suitable trajectory and marking the trajectory using a laser beam that intersects extends from the incision point of the patient, the surgeon, in step 910, connects a flexible arm 42 to a preparation cannula 46 via a clamp 44 and moves the assembly into the vicinity of the surgical site 12, as shown in FIG. 10A. The preparation cannula 46 guides instruments used to prepare the pedicle 120 for receiving a pedicle screw. Preferably, the incision point for a pedicle screw trajectory is at the junction of the pars interarticularis, the superior articular facet and the transverse process, though one skilled in the art will recognize that any suitable location can be used as the incision point.

Figure 10B:
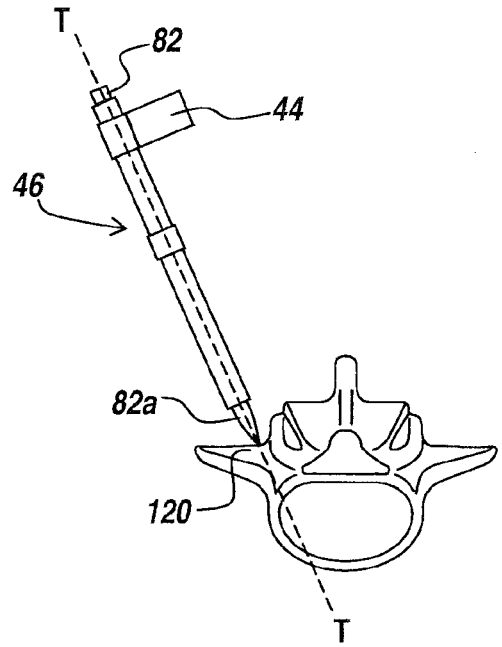

In step 920, the surgeon aligns the cannula 46 with the trajectory using a first instrument. The surgeon aligns the cannula 46 by guiding an obturator/awl 82 through the cannula 46 to the incision point, such that the tip 82a of the instrument touches the laser dot produced by the laser at the incision point. Then, the surgeon aligns the cannula 46 with the laser beam. As shown in FIG. 10B, the illustrative obturator/awl 82 includes a pointed tip 82a suitable for punching through the cortical wall of the patient to create a path, aligned with the trajectory, down the muscle plane to the facet. Alternatively, the surgeon inserts the obturator/awl 82 prior to moving the assembly towards the surgical site, then aligns the cannula using the point 82a of the obturator/awl 82.

In step 930, the surgeon continues to guide the first instrument, illustrated as the obturator/awl 82, through the aligned cannula until the tip 82a punches through cortical wall to begin the incision.

Figure 10C:
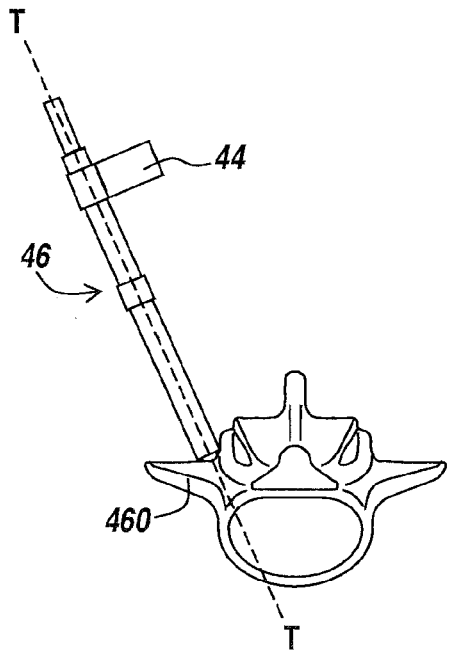

In step 940, while maintaining the obturator/awl 82 in alignment with the laser, the surgeon advances the cannula 46 over the obturator/awl 82 towards the surgical site, as shown in FIG. 10C. In the illustrative embodiment, the surgeon advances the cannula until the teeth 460 formed on the distal end of the cannula engage the vertebral facet.

Alternatively, the surgeon first punches through the cortical wall using the obturator/awl separate from the cannula 46, aligns the obturator with the trajectory using the laser and slides the cannula 46 over the aligned obturator to align the cannula 46 and create the initial incision at the surgical site.

After assuring that the cannula 46 is still aligned with the laser and making proper adjustments, if necessary, the surgeon locks the flexible arm 42 to fix the position of the cannula 46 relative to the surgical site in step 950.

Figure 10D:
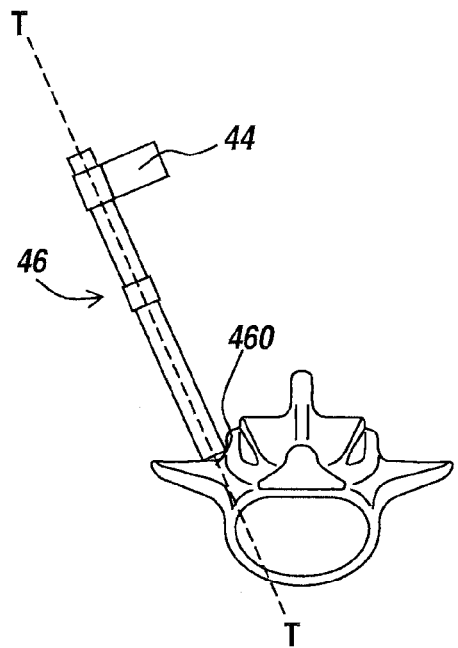

In step 960, the surgeon removes the obturator/awl 82, leaving the cannula 46 in the selected orientation, as shown in FIG. 10D.

In an optional step 970, the surgeon inserts a drill or probe through the cannula 46 to drill or probe a hole along the trajectory through the center of the pedicle. The drill or probe is sized and configured to fit the path defined through the cannula 46, and advance along the trajectory, guided by the cannula. The close fit between the cannula and the instrument prevents the instrument from deviating from the trajectory.

Figure 10E:
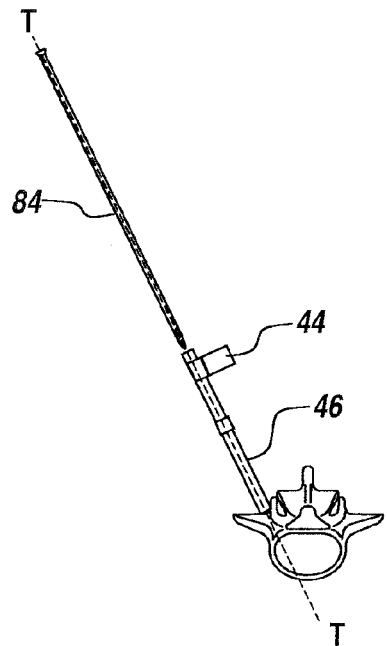

In step 980, the surgeon performs a bone tap using the cannula 46 to guide the path of the bone tap instrument used to perform the bone tap. To perform the bone tap, the surgeon inserts a bone tap 84 through the cannula 46, as shown in FIG. 10E, taps the pedicle and removes the tap from the cannula. During the bone tap, the cannula 46 constrains the motion of the bone tap 84 along the trajectory, preventing the bone tap from removing bone that outside of the trajectory.

Figure 10F:
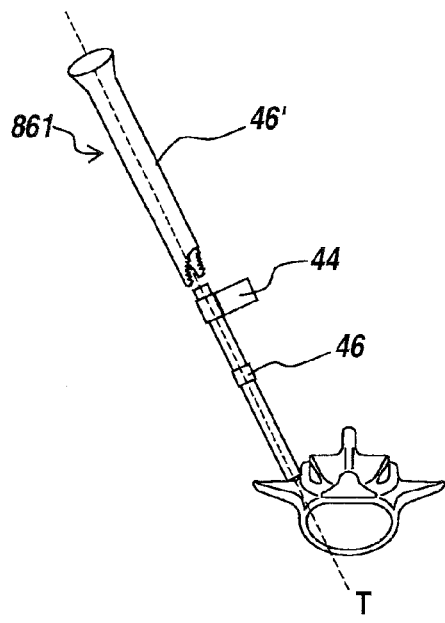
Figure 10G:
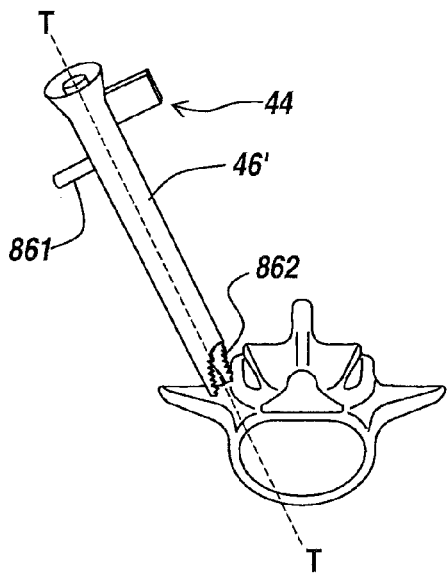
Figure 10H:
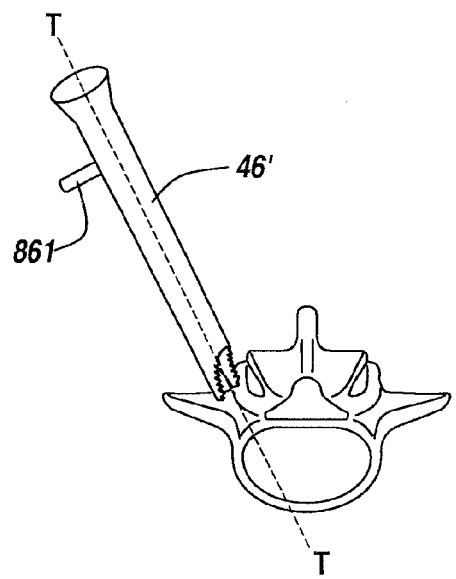

In step 990, the surgeon replaces the preparation cannula 46 with a larger insertion cannula used to insert a pedicle screw along the trajectory while holding back the tissue in the vicinity of the insertion site. As shown in FIGS. 10E-10H, the surgeon replaces the cannula 46 by sliding the C-shaped insertion cannula 46' over the cannula 46, as shown in FIG. 10F, and securing insertion cannula teeth 862 to the transverse process, as shown in FIG. 10G. While the cannula 46 maintains the position of the insertion cannula 46' in alignment with the trajectory, the user detaches the cannula 46 from the clamp 44 and attaches the clamp 44 to an attachment site 861 on the insertion cannula 46'. If necessary, the surgeon recalibrates the trajectory. Then, the user removes the cannula 46, leaving the insertion cannula 46' defining the trajectory T-T, as shown in FIG. 10H.

The insertion cannula 46' has a larger diameter than the cannula 46, suitable for dilating and retracting the tissue in the vicinity of the insertion site, which further opens and exposes the surgical site to facilitate insertion of a pedicle screw.

Finally, in step 998, surgeon inserts a pedicle screw through the insertion cannula 46', as shown in FIG. 10H, such that the pedicle screw aligns with the trajectory. The surgeon inserts the pedicle screw by inserting the stem of a pedicle screw through the incision site made in step 930 and into the hole defined by the bone tap in step 980. Using a screwdriver inserted through the insertion cannula 46', the surgeon then secures the pedicle screw to the pedicle.

According to an alternate embodiment, the preparation cannula 46 is used to both prepare the pedicle and insert the pedicle screw without using a tissue retractor.

The guidance system 100 can include a single uniformly sized cannula sized and dimensioned to receive and guide all instruments used in preparing a pedicle and inserting a screw into the pedicle along a trajectory. For example, all instruments used in the preparation and insertion process can have an outer diameter approximately equal to the inner diameter of the cannula. Alternatively, the guidance system 100 can include a plurality of cannulas, each sized and dimensioned to receive and guide a selected subset of instruments. For example, a first cannula, i.e., a pedicle preparation cannula, can be sized and configured to receive and guide a first subset of instruments used in the pedicle preparation process, such as the probe, drill and tap. A second cannula, i.e., a screw insertion cannula, can be sized and dimensioned to receive and guide a second subset of instruments, for example, the screw driver, used to insert a screw into the pedicle. In another embodiment, a guidance system includes only a pedicle prep cannula, allowing the surgeon to subsequently insert the screw without guidance.

According to another embodiment of the invention, the process of preparing for and inserting a pedicle screw can omit the step of tapping the bone in step 980 when the cannula 46 is used to insert self-tapping pedicle screws. In this embodiment, the surgeon defines a suitable trajectory, aligns the cannula with the trajectory and secures the cannula 46 in a fixed orientation in alignment with the trajectory, as described above. Then, the surgeon inserts a self-tapping screw along the trajectory under the guidance of the cannula 46 sized and shaped to receive and guide a screwdriver for screwing the self-tapping screw in place.

Those skilled in the art should recognize that there are many different types of cannulas and many different ways in which cannulas could be used. For example, a cannula could be rigid, semi-rigid, or flexible and could be configured in any number of different forms, such as a catheter, needle, endoscope, implement inserter, etc.

The use of a rigid lock for locking a trajectory guide into a selected position aligned with a suitable trajectory provides significant advantages over prior systems and methods for guiding instruments during a medical procedure. By maintaining the trajectory guide position with a rigid arm, image guidance is not required and therefore, the guide system does not require the continued use of a tracking marker after initial alignment of the trajectory guide with the cannula. Once the trajectory has been determined, the tracking marker is no longer used while guiding instruments to the working space. The use of a rigidly fixed cannula further eliminates the need for guide wires to maintain a selected trajectory, which tend to advance in the patient, causing injury, and are not as accurate.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A method for guiding a pedicle screw for a patient having a body, comprising the steps of:
   determining a suitable trajectory for inserting the pedicle screw into a pedicle of the patient;
   fixing the trajectory relative to a patient using a trajectory guide, wherein the trajectory guide is fixed at a fixation point outside the body of the patient, wherein fixing the trajectory comprises:
      positioning a flexible arm relative to the patient, wherein the flexible arm has a plurality of segments that are pivotally connected by joints, including at least one ball joint;
      fixing a position of the flexible arm by locking the joints of the flexible so that the joints will not pivot from their current positions;
      holding a cannula in a clamp that is coupled to the flexible arm, wherein the cannula serves as the trajectory guide for the trajectory; and
      locking a position of the cannula relative to the flexible arm via a cannula lock when the cannula is properly positioned to be aligned along the trajectory; and
   passing the pedicle screw through the cannula so that the pedicle screw may be implanted into the pedicle of the patient.

2. The method of claim 1, further comprising the step of inserting an instrument along the trajectory using the trajectory guide, wherein the trajectory guide constrains the movement of instrument along the trajectory.

3. The method of claim 1, wherein said determining a suitable trajectory comprises one of using a guide wire, using a laser, using a fluoroscopy unit, using an image-guided surgery unit and combinations thereof.

4. The method of claim 1, further comprising the step of aligning the trajectory guide with the trajectory prior to said fixing.

5. The method of claim 4, wherein the step of aligning the trajectory guide comprises:
   bringing the trajectory guide into a vicinity of a surgical site for receiving the implant; and
   moving the trajectory guide until an orientation marker marking the trajectory passes through and aligns with a path extending through the trajectory guide.

6. The method of claim 1, further comprising moving an instrument along the trajectory by inserting the instrument through the cannula.

7. The method of claim 6, wherein inserting the instrument comprises inserting the instrument into a channel of the trajectory guide and moving the channel along the trajectory using a track.

* * * * *